United States Patent [19]
Howard et al.

[11] Patent Number: 5,549,002
[45] Date of Patent: Aug. 27, 1996

[54] METHOD FOR DETECTING AND CHARACTERIZING FLAWS IN ENGINEERING MATERIALS

[75] Inventors: Patrick J. Howard, Cincinnati, Ohio; Richard Y. Chiao, Clifton Park, N.Y.

[73] Assignee: General Electric Company, Schenectady, N.Y.

[21] Appl. No.: 272,971

[22] Filed: Jul. 1, 1994

[51] Int. Cl.$^6$ ........................................... G01N 29/06
[52] U.S. Cl. ..................... 73/602; 73/620; 364/508; 364/507; 367/104
[58] Field of Search .................... 73/619, 620, 621, 73/628, 629, 634, 618, 627, 602; 364/508, 507; 367/104

[56] References Cited

U.S. PATENT DOCUMENTS

| | | | |
|---|---|---|---|
| 4,252,022 | 2/1981 | Hurwitz | 73/582 |
| 4,597,292 | 7/1986 | Fujii et al. | 73/599 |
| 4,730,495 | 3/1988 | Green | 73/620 |
| 4,841,489 | 6/1989 | Ozaki et al. | 367/104 |
| 4,862,892 | 9/1989 | Green | 73/620 |
| 5,065,763 | 11/1991 | Green et al. | 73/620 |

OTHER PUBLICATIONS

"A New System for Real–Time Synthetic Aperture Ultrasonic Imaging" by Yoshihiko Ozaki, et el, IEEE Transactions on Ultrasonics, Ferroelectrics, and Frequency Control, vol. 35, No. 6, Nov. 1988, pp. 828–838.

Primary Examiner—Hezron E. Williams
Assistant Examiner—Rose M. Finley
Attorney, Agent, or Firm—David C. Goldman; Marvin Snyder

[57] ABSTRACT

A method for detecting and characterizing flaws in an object having an arbitrary-shaped geometry. The present invention uses a synthetic aperture focusing technique (SAFT) which enables maximum aperture imaging. Maximum aperture imaging is attained by determining whether a plurality of reconstruction points within an object are in the width of a transmitted ultrasonic sound wave.

9 Claims, 4 Drawing Sheets 5,549,002

METHOD FOR DETECTING AND CHARACTERIZING FLAWS IN ENGINEERING MATERIALS

BACKGROUND OF THE INVENTION

The present invention relates generally to the nondestructive evaluation of engineering materials, and more particularly to the use of ultrasonic synthetic aperture focusing technique for detecting and characterizing flaws in engineering materials having planar and non-planar geometries.

Nondestructive evaluation (NDE) of engineering materials for flaws is an important step in ensuring product quality. A commonly used NDE technique is ultrasonic inspection. Typically, in ultrasonic inspection, an ultrasonic transducer scans the surface of the engineering material, sending either a focused or unfocused ultrasound beam towards the material. The transducer receives an ultrasound beam reflecting from the material. The maximum ultrasound signals are recorded to form a C-scan image and then compared to a threshold. If the maximum ultrasound signals exceed the threshold, then an alarm is activated. C-scan imaging provides simple and high quality images, however there are some limitations. For example, the lateral resolution of C-scan images is inversely proportional to the diameter of the transducer. Since the diameter of the transducer cannot be made arbitrarily large due to the accompanying increase in capacitance, the resolution in C-scan images will be limited. Another limitation is that the depth of field is relatively small for high resolution images, so mechanical scanning of multiple transducers focused at different depths is necessary to inspect thick sections of material.

Many of the limitations of C-scan imaging are circumvented by using a synthetic aperture focusing technique (SAFT). The idea behind SAFT is to synthesize an aperture by coherently combining the data generated at a plurality of scanning positions. In a typical SAFT implementation, a series of A-scans (i.e., RF wave forms representing echoes) are generated from different scanning positions. Subsequently, the A-scans are coherently combined to form focused images of the object's interior. The coherent combination is generally performed either in the spatial-frequency domain using a wave-theoretic approach or in the time-domain using the delay-and-sum approach. The effective aperture of a SAFT reconstruction is determined by the scanning positions that contribute to each reconstruction point. Thus, a wider beam pattern results in a larger effective SAFT aperture. Since SAFT imaging achieves focusing by processing the digitized wave form data, mechanical scanning is not necessary to image several depths as in C-scan imaging. However, a problem with present SAFT implementations is that they are limited to the detection and characterization of flaws in planar or simple geometries. Many NDE problems, especially those found in aerospace involve parts of complex geometry and the conventional SAFT implementations are unable to image these geometries because of transducer imaging limitations.

SUMMARY OF THE INVENTION

Therefore, it is a primary objective of the present invention to provide a method for detecting and characterizing flaws in engineering materials having non-planar, complex geometries.

Another object of the present invention is to use the principles of SAFT to attain the largest possible (i.e., maximum) aperture permitted by part geometry and the transducer for detecting and characterizing flaws in engineering materials having arbitrary-shaped geometries.

Thus, in accordance with the present invention, there is provided a method for detecting and characterizing flaws in an object having an arbitrary geometry. The method comprises scanning the object surface with a transducer transmitting ultrasonic sound waves at a plurality of scanning positions along the object surface. The ultrasonic sound waves have a cone-shaped volume defined by a half-angle θ, a starting radius $\rho_l$ located a predetermined distance below the transducer point of focus and an ending radius $\rho_h$ having a radius larger than the starting radius $\rho_l$, and a vertex formed at the transducer point of focus. The ultrasonic sound waves reflected from the object are detected with the transducer at each scanning position. The detected sound waves contain signals from the volume of the object which are represented by a discrete set of points, wherein the discrete set of points are a plurality of reconstruction points. Each reconstruction point is separated from the transducer point of focus by a distance $\rho_{ij}$ and has an angle $\theta_{kj}$ formed therebetween. The next step is to determine in accordance with $\rho_{ij}$ and $\theta_{kj}$, whether each of the plurality of reconstruction points is within the transducer aperture for a given scanning position. An image of the object's interior is formed by combining the data from the scanning positions within the aperture for each reconstruction point. The reconstructed image is then displayed for detection of flaws.

While the present invention will hereinafter be described in connection with a preferred embodiment and method of use, it will be understood that it is not intended to limit the invention to this embodiment. Instead, it is intended to cover all alternatives, modifications and equivalents as may be included within the spirit and scope of the present invention as defined by the appended claims.

DETAILED DESCRIPTION OF THE PRESENT INVENTION

Figure 1:
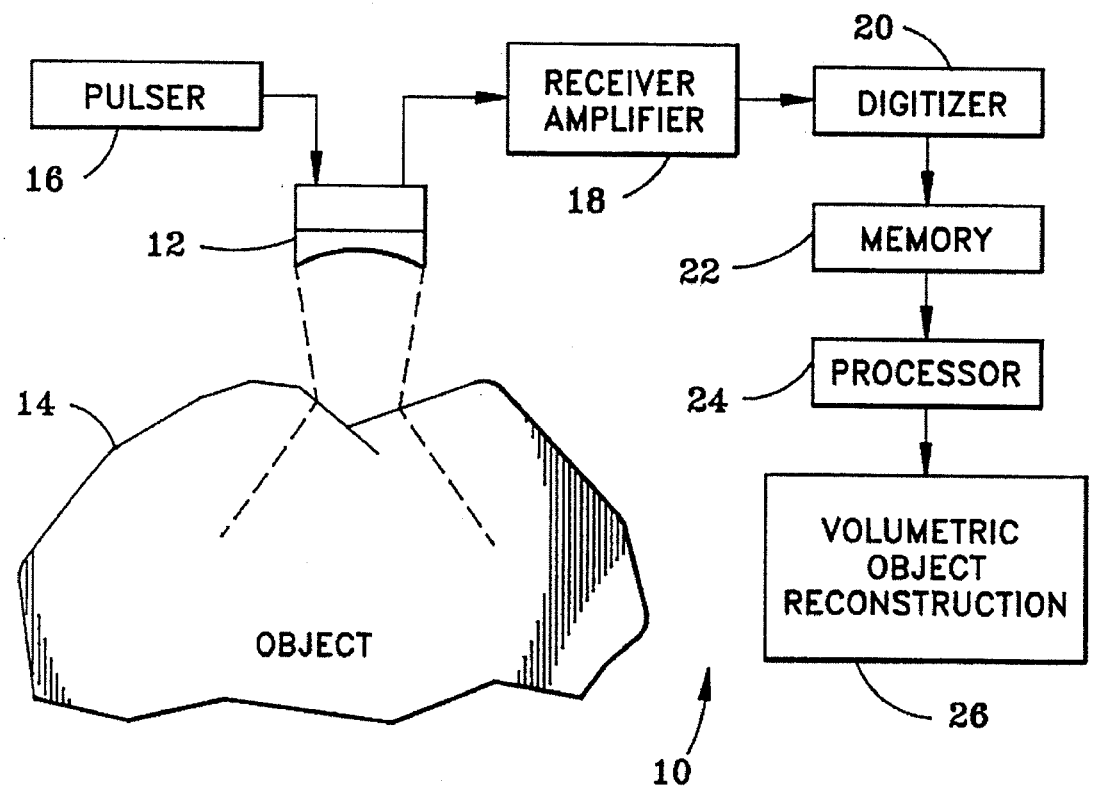
FIG. 1 is a block diagram of an ultrasonic inspection system used in the present invention.

FIG. 1 shows a block diagram of an ultrasonic inspection system 10 used in the present invention. In the ultrasonic inspection system, a transducer 12 is scanned over the surface of an object 14 having an arbitrary-shaped geometry. The transducer transmits an ultrasonic wave beam generated from a pulser 16 towards the object at a plurality of scanning positions along the object surface. Ultrasonic sound waves reflected from the object 14 are detected by the transducer and amplified by an amplifier 18. The amplified sound waves are digitized by a digitizer such as an A/D converter 20 and stored in a memory 22. The ultrasonic sound waves stored in the memory are processed by a processor 24. The processor using the technique of the present invention, which is described later in further detail, reconstructs a volumetric image of the object that is displayed on a display 26. The volumetric image is used to detect and characterize flaws in the object.

Figure 2:
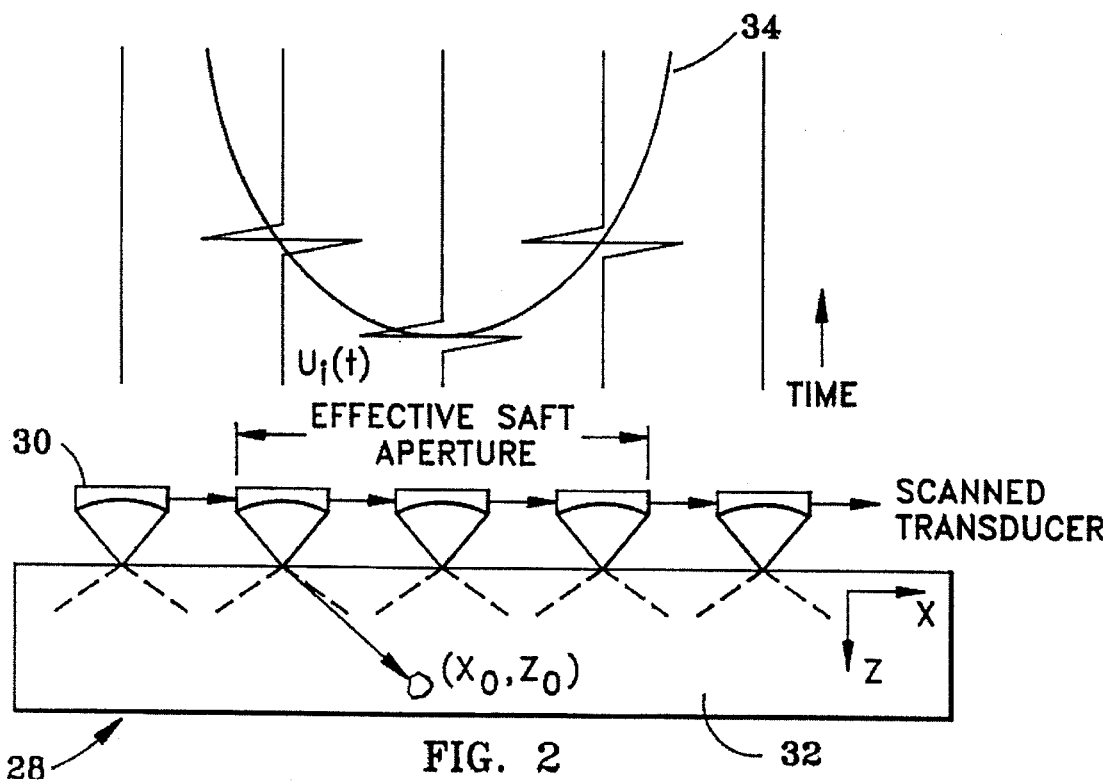
FIG. 2 is a diagram of a planar SAFT scanning configuration.

As mentioned earlier, SAFT has been used for detecting and characterizing flaws in objects having planar geometries. FIG. 2 shows a diagram of a planar SAFT scanning configuration 28. In the planar SAFT scanning configuration of FIG. 2, a single transducer 30 is scanned linearly in the x-direction over the surface of a part 32. However, for a cube-shaped part, the transducer is scanned in the y-direction. At each spatial position, the transducer transmits an ultrasonic sound wave into the part. The transducer receives a back scattered signal (i.e., an Δ scan) at a constant spatial interval Δx and Δy. The top portion of FIG. 2 shows the relationship between the transducer point of focus on the surface of the part and an acoustic reflector $(x_o, y_o, z_o)$ in the part that has a reflectivity $r(x_o, y_o, z_o)$. In particular, the time of flight t(x) between the transducer point of focus and the acoustic reflector is represented by a hyperbolic curve 34. At the first spatial interval Δx, the acoustic reflector $(x_o, y_o, z_o)$ is not within the transmitted ultrasonic sound wave and therefore a back scatter signal is not received. However, in the next three spatial intervals, the acoustic reflector $(x_o, y_o, z_o)$ is within the transmitted ultrasonic sound wave and back scatter signals are received. At the last spatial interval, the acoustic reflector $(x_o, y_o, z_o)$ is again not within the transmitted ultrasonic sound wave and a back scatter signal is not received. The image of the acoustic reflector is produced by coherently summing up the detected back scatter signals that are on the hyperbolic curve for all the acoustic reflectors within the object. In effect, the range of summation is determined by the width of the ultrasonic sound wave or the aperture of the transducer.

Figure 3A:
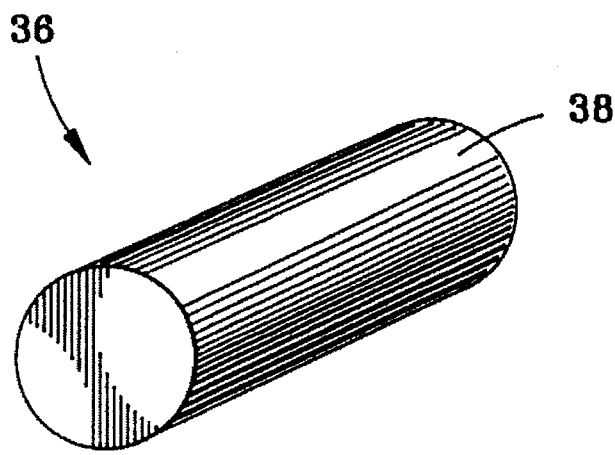
FIG. 3 is a schematic of NDE at the various manufacturing stages of an engine disk.
Figure 3B:
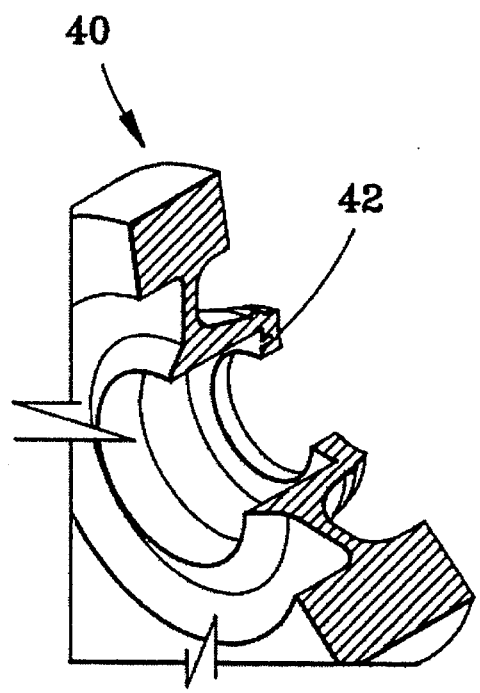
Figure 3C:
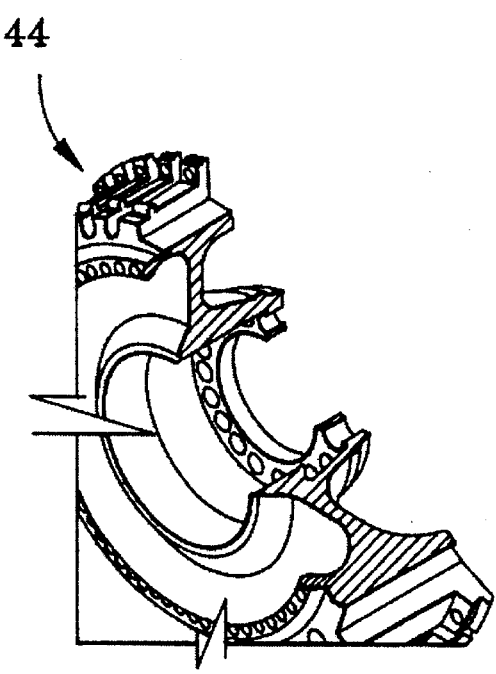

FIG. 3 is an example showing the importance of being able to image complex, arbitrary-shaped geometries. In particular, FIG. 3 shows a schematic of NDE at the various manufacturing stages of an engine disk. At the initial stage 36, a titanium billet 38 is inspected for flaws and defects. Conventional SAFT imaging is unable to image the billet because of its curved surface. In the next stage 40, the titanium billet 38 is forged into a sonic-shaped part 42. Since the sonic-shaped part has a complex, arbitrary geometry, the conventional SAFT is again ineffective for imaging the curved areas of the part. In addition, at the finished stage 44, the conventional SAFT imaging is ineffective for imaging the finished part which includes an outer bolt hole, an inner bolt hole, a bore and an aft web. Other complicated engine components that have complex, arbitrary shapes are blades and panels. The maximum aperture imaging technique of the present invention which is described below is capable of being used on engine parts such as disks, blades, and panels, and other complex, non-planar shaped geometries that undergo NDE inspection. In addition, the maximum aperture imaging technique is equally as effective imaging shapes having circular, elliptical, and cylindrical, etc., geometries.

Figure 4:
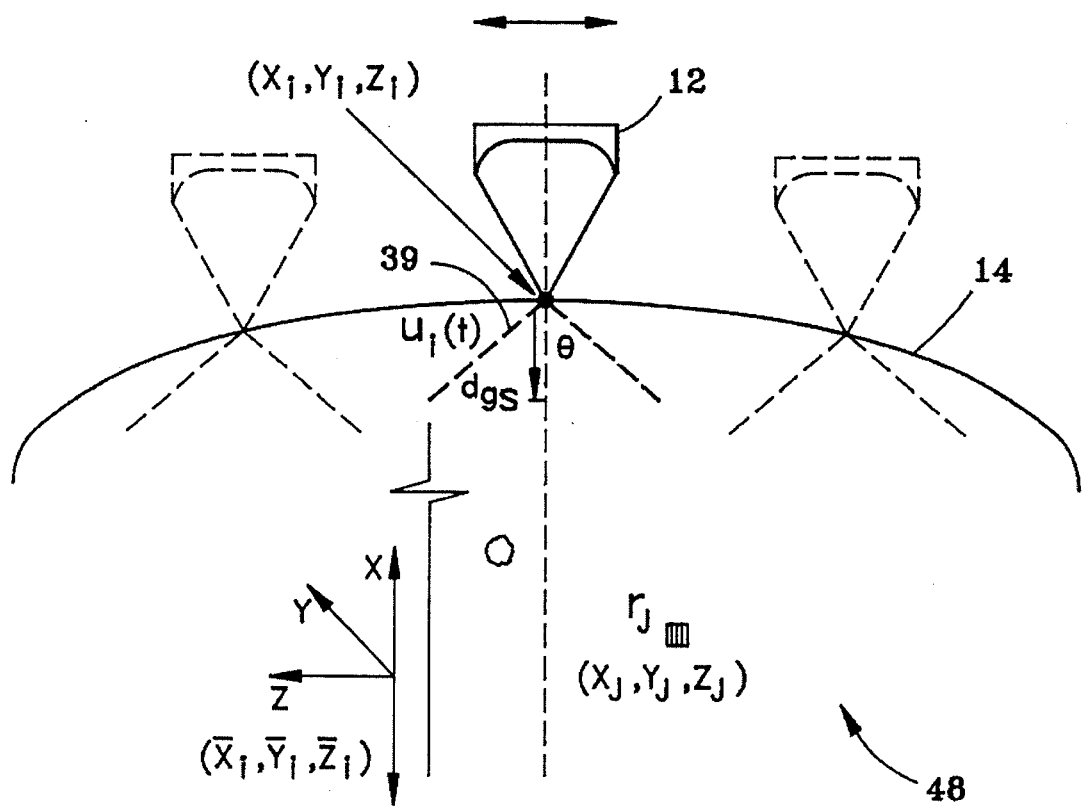
FIG. 4 is a diagram of a maximum aperture SAFT scanning configuration for arbitrary-shaped geometries.
Figure 5:
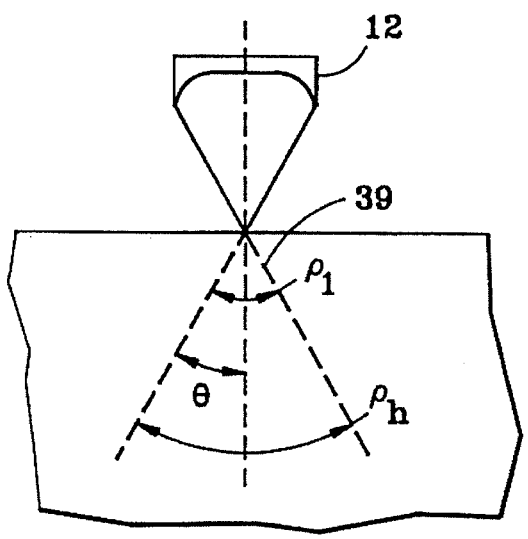
FIG. 5 is an illustration of a transducer beam geometry used in the present invention.

In order to image arbitrary-shaped surface geometries as in the present invention, the aperture of the transducer needs to be maximized. A maximum aperture uses the most information possible for image formation. In maximum aperture imaging, the largest possible aperture permitted by part geometry and the physical transducer is used to image each point in the object that is under inspection. FIG. 4 shows a diagram of a maximum aperture SAFT scanning configuration 48 for arbitrary-shaped geometries. In the present invention, the transducer 12 is scanned over the arbitrary-shaped surface of the object 14. The point of focus $(x_i, Y_i, z_i)$ of the transducer 12 as it is scanned over the surface, is oriented on an axis normal to the surface of the object 14. The point of focus is not necessarily on the surface but may be at the sub-surface above the region that is being imaged. At the point of focus, the transducer transmits an ultrasonic sound wave 39 that is assumed to approximate a beam geometry having a cone-shaped volume defined by a half-angle θ, a starting radius $\rho_l$ located a predetermined distance $d_{gs}$ below the transducer point of focus and an ending radius $\rho_h$ having a larger radius than the starting radius $\rho_l$, and a vertex formed at the transducer point of focus (see FIG. 5). The starting and ending radii are defined as follows:

$$\rho_l = d_{gs}$$

$$\rho_h = d_{gs} + \frac{t_s(T-1)c}{2}$$

where $d_{gs}$ is the start of the A-scan data at a given scanning position which is essentially the distance from the transducer point of focus to a point below the surface of the object where data collection begins; and $$\frac{t_s(T-1)c}{2}$$

is the length of material inspected by each A-scan where $t_s$ the sampling rate, T is the number of samples, and c is the velocity of sound, and 2 is the time accounting for the transmission and reflection of the sound waves at a given scanning position.

At each scanning position, the transducer detects ultrasonic waves reflected from the object at a velocity of sound c, at every $t_s$ seconds, starting at the distance $d_{gs}$ below the entry surface. The detected sound waves are a collection of sampled wave forms (i.e., A scans), $\{u_i(t): i \in D\}$ containing echoes from a plurality of reconstruction points $r_j$ in the interior of the object 14 that are collected at a location $(x_i, y_i, z_i)$. The reconstruction points are a discrete set of points within the object that are used for imaging the object. For each $u_i(t)$, the location of the point of focus $(x_i, y_i, z_i)$ and a unit transducer orientation vector $(\bar{x}_i, \bar{y}_i, \bar{z}_i)$ are known or can be calculated with respect to a global coordinate system, so the position of the transducer can be determined. In the present invention, the plurality of reconstruction points $r_j$ are reconstructed by the processor 24 which uses a delay-and-sum technique. The delay-and-sum technique may be either data-driven or reconstruction driven. In a data-driven technique, each data point is compared to the given set of reconstruction points and a decision is made about whether the point is within the transducer aperture. The reconstruction technique, which is preferred in the present invention, compares each reconstruction point with a set of data points and decides whether the reconstruction point is within the transducer aperture.

In order to determine whether a reconstruction point $r_j$ is within the aperture of a waveform $u_i(t)$, the first step is to compute the distance between the reconstruction point, $r_j$, and the transducer point of focus $(x_i, y_i, z_i)$, $\rho_{ij}$, for all $i \in D$. The distance $\rho_{ij}$ is defined as follows:

$$\rho_{ij} = \sqrt{(x_j - x_i)^2 + (y_j - y_i)^2 + (z_j - z_i)^2}$$

Then $\rho_{ij}$ is compared to $\rho_l$ and $\rho_h$. The points which satisfy:

$$\rho_l \leq \rho_{ij} \leq \rho_h$$

are separated into a set $\{u_k(t):k \in A_j\}$. Next, for all $k \in A_j$, the cosine of the angle $\theta_{kj}$ between the reconstruction point $r_j$ and the transducer axis is taken, using the following inner product $$\cos\theta_{kj} = \frac{(x_j - x_k)\overline{x_k} + (y_j - y_k)\overline{y_k} + (z_j - z_k)\overline{z_k}}{\rho_{kj}}$$

Then the cosine of $\theta_{kj}$ is compared to the cosine of $\theta$. The points which satisfy:

$$\cos\theta_{kj} \geq \cos\theta$$

are in the transducer aperture and are separated into a set $\{u_l(t):l \in A_j\}$. The time index $t_{lj}$ in the A scan that corresponds to the distance $\rho_{lj}$ is computed for all $\{u_l(t):l \in A_j\}$ using the following equation:

$$t_{lj} = \frac{2(\rho_{lj} - d_{gs})}{ct_s}$$

The value of the reconstruction point $r_j$ is determined by the following equations:

$$d_j = \frac{1}{N_j} \sum_{l \in A_j}^{N_j-1} w_l u_l(t_{lj}:t_{lj} + N_p)$$

where $d_j$ is an $N_p$ vector which is the length of an ultrasonic pulse, $N_j$ is the number of points in $A_j$, and $w_l$ is a weighing factor used to compensate the effects of the transducer ultrasonic sound wave. The value of the reconstruction point is obtained by match filtering $d_j$ with the transmitted pulse $P$ in the following manner:

$$r_j = d_j^T P$$

where T denotes vector transpose.

Figure 6A:
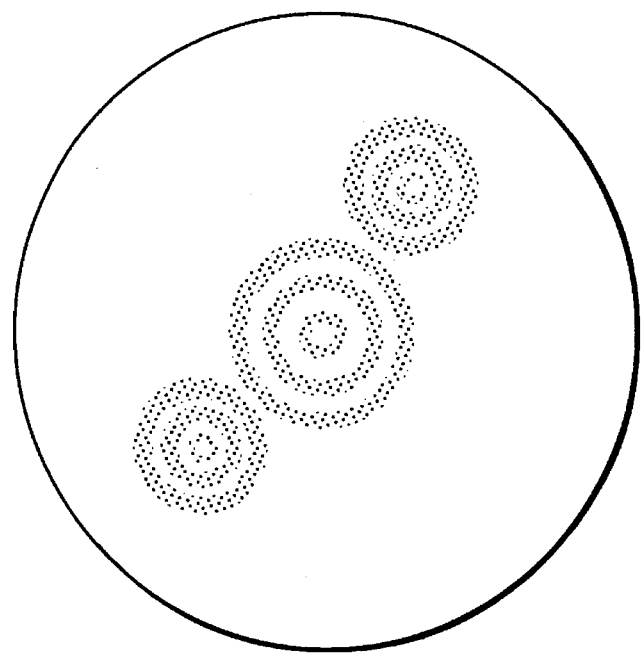
FIGS. 6a–6b are images derived from the maximum aperture SAFT of the present invention.
Figure 6B:
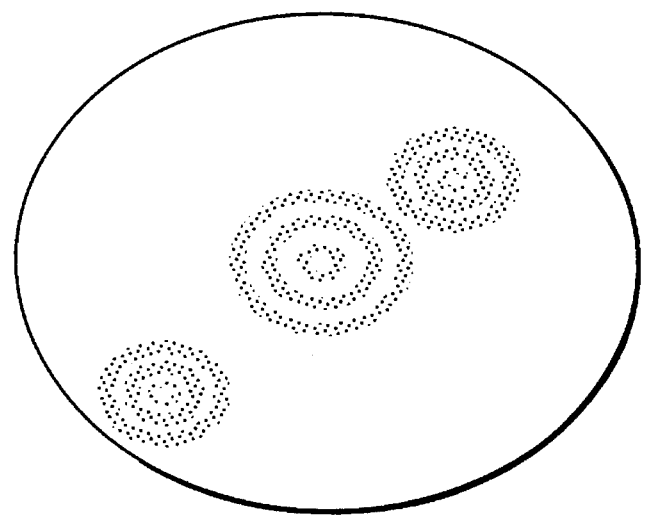

Essentially, the signals from each of the scanning positions that are within the transducer aperture for each reconstruction point are combined to form a reconstructed image of the arbitrary-shaped object. After all the reconstruction points have been processed by the processor 24, the reconstruction points are ordered into a volumetric image on the display 26. The displayed image is then used to detect and characterize flaws within the arbitrary-shaped object. Examples of images attained using the maximum aperture SAFT techniques of the present invention are shown in FIGS. 6a–6b. In both FIGS. 6a and 6b, three flaws are detected, with each flaw being equal in strength and having different amplitudes.

It is therefore apparent that there has been provided in accordance with the present invention, a method and apparatus for using SAFT for detecting and characterizing flaws in objects having an arbitrary-shaped geometry that fully satisfy the aims and advantages and objectives hereinbefore set forth. The invention has been described with reference to several embodiments, however, it will be appreciated that variations and modifications can be effected by a person of ordinary skill in the art without departing from the scope of the invention.

The invention claimed is:

1. A method for detecting and characterizing flaws in an object having an arbitrary-shaped geometry, comprising the steps of:

scanning a surface of the object with a transducer transmitting ultrasonic sound waves through an aperture at a plurality of scanning positions along an axis normal to the object surface, the transducer having a point of focus along the object surface that transmits ultrasonic sound waves having a cone-shaped volume defined by a half-angle $\theta$, a starting radius $\rho_l$ located a predetermined distance below the transducer point of focus and an ending radius $\rho_h$ having a radius larger than the starting radius $\rho_l$, and a vertex formed at the transducer point of focus;

detecting ultrasonic sound waves reflected from the object with the transducer at each scanning position, the detected sound waves containing signals from a volume of the object, the signals being a discrete set of points within the object representing a plurality of reconstruction points, each reconstruction point being separated from the transducer point of focus by a distance $\rho_{ij}$ and having an angle $\theta_{kj}$ formed therebetween;

determining in accordance with $\rho_{ij}$ and $\theta_{kj}$ whether each of the plurality of reconstruction points is within the transducer aperture for a given scanning position;

combining the signals from each of the scanning positions that are within the transducer aperture for each reconstruction point to form a reconstructed image of the arbitrary-shaped object; and displaying the reconstructed image and detecting flaws within the arbitrary-shaped object.

2. A method according to claim 1, wherein said step of determining includes comparing the distance $\rho_{ij}$ to the starting radius $\rho_l$ and to the ending radius $\rho_h$ and determining whether $\rho_l \leq \rho_{ij} \leq \rho_h$.

3. A method according to claim 2, further including comparing the computed angle $\theta_{kj}$ to $\theta$ for points satisfying $\rho_l \leq \rho_{ij} \leq \rho_h$, the reconstruction point being within the transducer aperture if $\cos\theta_{kj} \geq \cos\theta$.

4. A method according to claim 3, further including determining a time index for each of the reconstruction points within the transducer aperture.

5. A method according to claim 4, further including summing each of the reconstruction points within the transducer aperture in accordance with the time index.

6. A method for detecting and characterizing flaws in an object having an arbitrary-shaped geometry, comprising the steps of:

scanning a surface of the object with a transducer transmitting ultrasonic sound waves through an aperture at a plurality of scanning positions along an axis normal to the object surface, the transducer having a point of focus along the object surface that transmits ultrasonic sound waves having a cone-shaped volume defined by a half-angle $\theta$, a starting radius $\rho_l$ located a predetermined distance below the transducer point of focus and an ending radius $\rho_h$ having a radius larger than the starting radius $\rho_l$, and a vertex formed at the transducer point of focus;

detecting ultrasonic sound waves reflected from the object with the transducer at each scanning position, the detected sound waves containing signals from a volume of the object, the signals being a discrete set of points within the object representing a plurality of reconstruction points, each reconstruction point being separated from the transducer point of focus by a distance $\rho_{ij}$ and having an angle $\theta_{kj}$ formed therebetween;

determining in accordance with $\rho_{ij}$ and $\theta_{kj}$ whether each of the plurality of reconstruction points is within the transducer aperture for a given scanning position, said step of determining includes comparing the distance $\rho_{ij}$ to the starting radius $\rho_l$ and to the ending radius $\rho_h$, and comparing the computed angle $\theta_{kj}$ to $\theta$ for points satisfying $\rho_l \leq \rho_{ij} \leq \rho_h$, the reconstruction points being within the transducer aperture if $\cos \theta_{kj} \geq \cos \theta$:

combining the signals from each of the scanning positions that are within the transducer aperture for each reconstruction point to form a reconstructed image of the arbitrary-shaped object; and displaying the reconstructed image and detecting flaws within the arbitrary-shaped object.

7. A method according to claim 6, further including determining a time index for each of the reconstruction points within the transducer aperture.

8. A method according to claim 7, further including summing each of the reconstruction points within the transducer aperture in accordance with the time index.

9. A method for detecting and characterizing flaws in an object having an arbitrary-shaped geometry, comprising the steps of:

scanning a surface of the object with a transducer transmitting ultrasonic sound waves through an aperture at a plurality of scanning positions along an axis normal to the object surface, the transducer having a point of focus along the object surface that transmits ultrasonic sound waves having a cone-shaped volume defined by a half-angle $\theta$, a starting radius $\rho_l$ located a predetermined distance below the transducer point of focus and an ending radius $\rho_h$ having a radius larger than the starting radius $\rho_l$, and a vertex formed at the transducer point of focus;

detecting ultrasonic sound waves reflected from the object with the transducer at each scanning position, the detected sound waves containing signals from a volume of the object, the signals being a discrete set of points within the object representing a plurality of reconstruction points, each reconstruction point being separated from the transducer point of focus by a distance $\rho_{ij}$ and having an angle $\theta_{kj}$ formed therebetween;

determining in accordance with $\rho_{ij}$ and $\theta_{kj}$ whether each of the plurality of reconstruction points is within the transducer aperture for a given scanning position, said step of determining includes comparing the distance $\rho_{ij}$ to the starting radius $\rho_l$ and to the ending radius $\rho_h$, and comparing the computed angle $\theta_{kj}$ to $\theta$ for points satisfying $\rho_l \leq \rho_{ij} \leq \rho_h$, the reconstruction points being within the transducer aperture if $\cos \theta_{kj} \geq \cos \theta$, combining the signals from each of the scanning positions that are within the transducer aperture for each reconstruction point to form a reconstructed image of the arbitrary-shaped object, said step of combining includes determining a time index for each of the reconstruction points within the transducer aperture and summing each of the reconstruction points within the transducer aperture in accordance with the time index; and displaying the reconstructed image and detecting flaws within the arbitrary-shaped object.

* * * * *